United States Patent
Jones

(10) Patent No.: US 11,311,701 B2
(45) Date of Patent: Apr. 26, 2022

(54) TUBE STABILISING DEVICE

(71) Applicant: UNIVERSITY OF CENTRAL LANCASHIRE, Preston (GB)

(72) Inventor: Martin J. Jones, Lancashire (GB)

(73) Assignee: UNIVERSITY OF CENTRAL LANCASHIRE, Preston (GB)

( * ) Notice: Subject to any disclaimer, the term of this patent is extended or adjusted under 35 U.S.C. 154(b) by 467 days.

(21) Appl. No.: 16/321,190

(22) PCT Filed: Jul. 27, 2017

(86) PCT No.: PCT/GB2017/052194
§ 371 (c)(1),
(2) Date: Jan. 28, 2019

(87) PCT Pub. No.: WO2018/020253
PCT Pub. Date: Feb. 1, 2018

(65) Prior Publication Data
US 2019/0160262 A1    May 30, 2019

(30) Foreign Application Priority Data
Jul. 29, 2016    (GB) ..................................... 1613154

(51) Int. Cl.
*A61M 5/32* (2006.01)
*A61M 25/02* (2006.01)
*F16M 13/04* (2006.01)

(52) U.S. Cl.
CPC ....... *A61M 25/02* (2013.01); *A61M 2025/024* (2013.01); *A61M 2025/028* (2013.01); *F16M 13/04* (2013.01)

(58) Field of Classification Search
CPC ...... A61M 2025/024; A61M 2025/028; A61M 25/02; A61M 25/0213
See application file for complete search history.

(56) References Cited

U.S. PATENT DOCUMENTS 4,666,434 A   5/1987  Kaufman
5,188,609 A * 2/1993  Bayless ................. A61M 25/02
                                                          604/174

(Continued)

FOREIGN PATENT DOCUMENTS

KR        101583712 B     1/2016
WO          9956802 A1   11/1999
WO       2014190424 A1    4/2014

OTHER PUBLICATIONS

International Search Report and Written Opinion, European Patent Office, PCT/GB2017/052194, dated Nov. 8, 2017, 18 pages.

(Continued)

*Primary Examiner* — Rebecca E Eisenberg
(74) *Attorney, Agent, or Firm* — Taft Stettinius & Hollister LLP; Stephen F. Rost

(57) ABSTRACT

A tube stabilising device (10, 20, 30) for a tube attached to a patient, comprising a base member (110, 210, 310) fixable to a surface, the base member having a support surface (112, 212, 312) for supporting the base member on a surface of the patient. The tube stabilising device further comprising a tube retaining member (120, 220, 320). The base member includes a cavity (114, 214, 314) configured to receive a flange (122, 222, 322) of the tube retaining member such that, when received, the cavity at least partially overlaps the flange so that the flange is retained by the base member, the tube retaining member is moveably attached to the base member and the flange is moveable within the cavity in any direction parallel to the support surface. The tube retaining member is configured to retain a tube extending from the patient such that, when retained, the tube is moveable relative to the base member.

23 Claims, 3 Drawing Sheets

(56) References Cited

U.S. PATENT DOCUMENTS

| | | | | |
|---|---|---|---|---|
| 5,916,199 | A * | 6/1999 | Miles | A61M 25/02 |
| | | | | 604/174 |
| 5,944,696 | A * | 8/1999 | Bayless | A61M 25/02 |
| | | | | 604/174 |
| 6,287,281 | B1 | 9/2001 | Nishtala et al. | |
| 9,821,144 | B2 * | 11/2017 | Mouri | A61M 25/02 |
| 2006/0047268 | A1 * | 3/2006 | Stephens | A61M 25/0041 |
| | | | | 604/533 |
| 2007/0066958 | A1 | 3/2007 | Wright | |
| 2014/0228810 | A1 * | 8/2014 | Rosenberg | A61M 25/02 |
| | | | | 604/513 |
| 2015/0250984 | A1 * | 9/2015 | Humphries | A61M 25/02 |
| | | | | 604/180 |
| 2016/0296725 | A1 | 10/2016 | Calco | |
| 2019/0015635 | A1 * | 1/2019 | Rosenhan | A61M 25/02 |

OTHER PUBLICATIONS

U.K. Search Report, U.K. Intellectual Property Office, GB1613154.2, dated Jan. 31, 2017, 3 pages.

\* cited by examiner

TUBE STABILISING DEVICE

This application is a U.S. national stage application under 35 U.S.C. 0371 of PCT International Application Serial No. PCT/GB2017/052194, which has an international filing date of Jul. 27, 2017, designates the United States of America, and claims the benefit of GB Application No, 1613154.2, which was filed on Jul. 29, 2016, the disclosures of which are hereby expressly incorporated by reference in their entirety.

This invention relates to a tube stabilising device for a tube attached to a patient.

BACKGROUND

Intravenous (IV) cannulation is a common clinical procedure in which a thin tube (cannula) is inserted into a patient's vein to provide venous access for blood sampling and administering fluids, medications and the like. The cannula may come with a trocar attached which allows puncturing of the patient in order to insert the cannula. Most commonly, the entry site for a cannula is a vein at the joint between a patient's hand and their forearm, such that the cannula extends from the patient's vein in a direction towards the end of the patient's hand. Typically, adjacent to the entry site of the cannula, the cannula is forced into a U-shape and fixed to the patient's hand. The cannula, due to the U-shape, may double back on itself to extend down the patient's forearm and be fixed to the patient's forearm to further secure the cannula. Adhesive tape or sutures may be used to fix the cannula to the patient. The elastic nature of the cannula may exert a constant force on the cannula to straighten and, if the cannula is not fixed correctly, such a force may exert unwanted forces on the entry site of the cannula.

Further, and even if the cannula is fixed correctly to the patient, when the patient moves or twists their arm whilst the cannula is fixed to their skin, unwanted forces may be applied at the cannula entry site due to the cannula moving relative to the cannula entry site. Such unwanted forces may result in patient discomfort and, in some cases, bruising and swelling of the patient's hand at the cannula entry site. As a result of such bruising or swelling, it is possible for the patient to suffer from occlusion or phlebitis. Further, such movement or twisting of the patient's arm may lead to inadvertent dislodging of the cannula.

It is an object of certain embodiments of the present invention to address some of the above described disadvantages associated with the prior art.

It is also an object of certain embodiments of the present invention to address some of the general disadvantages associated with fixing tubes, which are attached to a patient (e.g. a nasal cannula or a catheter), to a surface (e.g. a patient's skin).

BRIEF SUMMARY OF THE DISCLOSURE

According to a first aspect of the present invention, there is provided a tube stabilising device for a tube attached to a patient, comprising:
 a base member fixable to a surface; and
 a tube retaining member moveably attachable to the base member;
 wherein the tube retaining member is configured to retain a tube extending from the patient such that, when retained, the tube is moveable relative to the base member.

In certain embodiments, the tube may comprise a cannula or catheter.

In certain embodiments, the surface may comprise a surface of a patient.

In certain embodiments, the base member may have a support surface for supporting the base member on a surface of the patient, and the tube retaining member is moveably attachable to the base member so as to be moveable in at least one direction substantially parallel to the support surface. The tube retaining member may be moveably attachable to the base member so as to be moveable in at least two mutually orthogonal directions substantially parallel to the support surface.

In certain embodiments, a first portion of the tube retaining member may be receivable by the base member such that, when the tube retaining member is received by the base member, the tube retaining member is moveably attached to the base member. The tube retaining member may include a second portion, the second portion being removeably attachable to the first portion of the tube retaining member.

In certain embodiments, the base member may include a cavity configured to receive the first portion of the tube retaining member such that, when received, the tube retaining member is moveably attached to the base member and the first portion of the tube retaining member is moveable within the cavity. The first portion of the tube retaining member may include a flange configured to be received by the cavity of the base member such that, when received, the flange is moveable within the cavity of the base member.

In certain embodiments, when the flange is received by the cavity of the base member, the cavity may at least partially overlap the flange so that the flange is retained by the base member.

In certain embodiments, the tube retaining member may include receiving means configured to receive a portion of the tube. The second portion of the tube retaining member may comprise the receiving means.

In certain embodiments, the receiving means of the tube retaining member may include a substantially straight portion such that, when the tube is received by the tube retaining member, the tube is substantially straight throughout the straight portion of the receiving means. The straight portion of the receiving means may include one or more clips configured to receive and retain the tube within the tube retaining member. The straight portion of the receiving means may include two or more clips along the same axis configured such that, when the tube is received by the tube retaining member, the tube is substantially straight between the two or more clips.

In certain embodiments, the receiving means may include a curved guide configured such that, when the tube is received by the receiving means, the tube is curved around the curved guide. The curved guide may include one or more clips configured to receive and retain the tube within the tube retaining member. The one or more clips of the curved guide may comprise one or more curved clips.

In certain embodiments, the receiving means may include a straight portion adjacent to a first end of the curved portion. The receiving means may further include a straight portion adjacent to an end opposite the first end of the curved portion.

In certain embodiments, the curved guide may comprise a U-shaped curve configured such that, when the tube is received by the receiving means, the tube is U-shaped within the curved guide.

In certain embodiments, the clip may be part-cylindrical. The curved clip may be part-cylindrical.

In certain embodiments, the base member may be fixable to the patient via an adhesive. The adhesive may comprise an adhesive attachment pad.

According to a second aspect of the present invention, there is provided a tube stabilising assembly for a tube inserted into a patient, comprising:

a first tube stabilising device according to any embodiment of the first aspect of the present invention; and one or more further tube stabilising device according to any embodiment of the first aspect of the present invention;

wherein the tube stabilising assembly is configured such that a tube exiting a patient's body is retainable by the first tube stabilising device and the one or more further tube stabilising device.

According to a third aspect of the present invention, there is provided a tube stabilising assembly for a tube inserted into a patient, comprising:

a first tube stabilising device according any embodiment of the first aspect of the present invention wherein the receiving means of the tube retaining portion includes a curved guide configured such that, when the tube is received by the receiving means, the tube is curved around the curved guide; and a second tube stabilising device according to any embodiment of the first aspect of the present invention wherein the receiving means of the tube retaining member includes a substantially straight portion such that, when the tube is received by the tube retaining member, the tube is substantially straight throughout the straight portion of the receiving means;

wherein the tube stabilising assembly is configured such that a tube exiting a patient's body is retainable by the first tube stabilising device and the second tube stabilising device.

In certain embodiments, the first tube stabilising device may be configured to attach to a patient's hand adjacent to an exit point of a tube from the patient's hand, and the second tube stabilising device may be configured to attach to the patient's forearm, the tube stabilising assembly being configured such that the tube is moveable within the assembly relative to the patient.

BRIEF DESCRIPTION OF THE DRAWINGS

Embodiments of the invention are further described hereinafter with reference to the accompanying drawings, in which.

DETAILED DESCRIPTION

Figure 1:
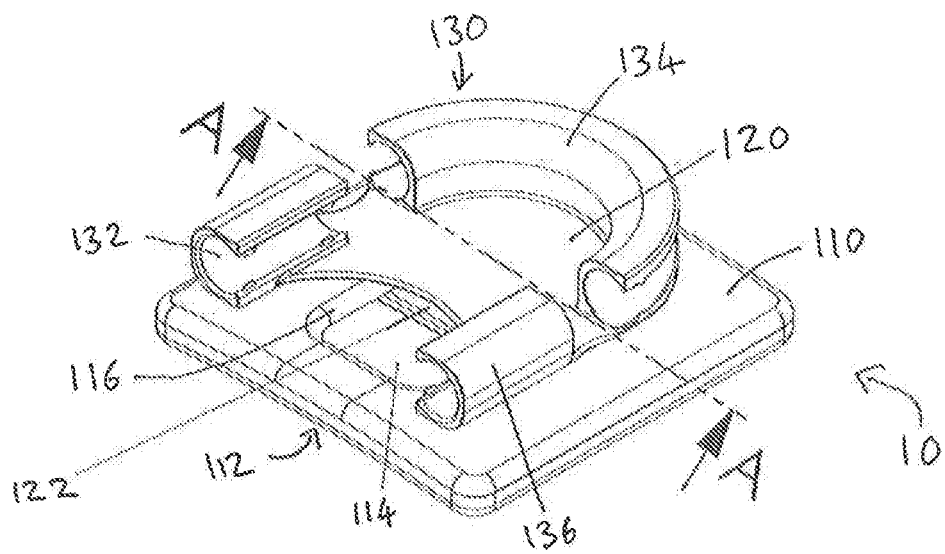
FIG. 1 is a perspective view of a tube stabilising device according to an embodiment of the present invention.

A tube stabilising device 10 for a tube attached to a patient in accordance with an embodiment of the present invention is shown in FIG. 1. The tube stabilising device 10 includes a base member 110 fixable to a surface, e.g. a patient, and a tube retaining member 120 moveably attached to the base member 110. The tube stabilising device 10 may be used for any tube suitable for inserting into or attaching to a patient. Throughout the present specification, the phrase "tube" is considered to encompass any hollow or non-hollow tubular member such as a catheter, a cannula, a hose, a wire, a cable, or other.

Figure 2:
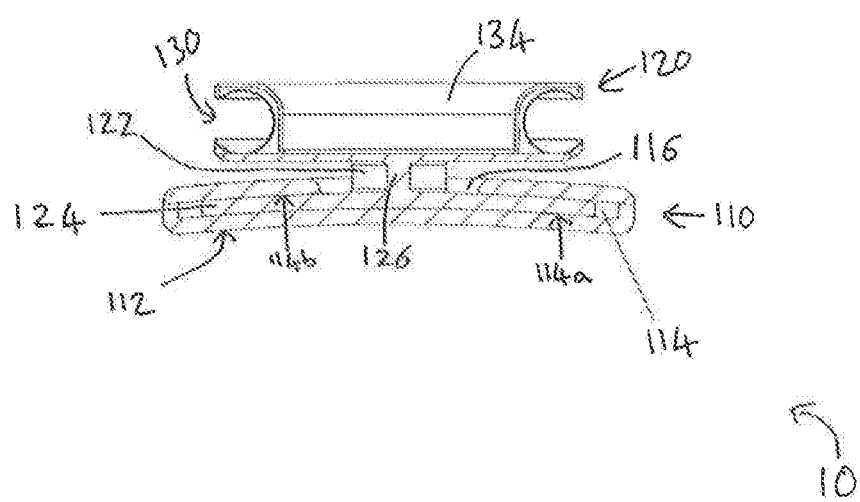
FIG. 2 is a sectional view along the line A-A of FIG. 1.

FIG. 2 shows a sectional view along the line A-A of FIG. 1. The base member 110 includes a support surface 112, a cavity 114 and a cavity opening 116. The support surface 112 is shaped such that it is suitable for supporting the base member 110 on a surface of the patient. In the embodiment shown in FIG. 2, the base member 110 is configured to be positioned on a curved surface of the patient's body, whereby the support surface 112 comprises a curvature suitable for fixing the base member 110 to a curved surface of the patient's body. The shape of the support surface 112 is not limited to the embodiment shown in FIG. 2. In other embodiments, the support surface 112 may comprise one or more flat surfaces. The cavity 114 has a bottom surface 114*a* which is substantially parallel to the support surface 112. In other embodiments, the bottom surface 114*a* may not be parallel to the support surface 112.

The tube retaining member 120 includes a flange 122 which is received by the base member 110 so that the tube retaining member 120 is moveably attached to the base member 110. The flange 122 has a distal portion 124 received by the cavity 114 of the base member 110, and a proximal portion 126 received by the cavity opening 116 of the base member 110. In the embodiment shown in FIG. 2, the distal portion 124 comprises a substantially planar surface and the proximal portion 126 comprises a stem extending orthogonal to the distal portion 126, such that the flange 122 comprises a T-shaped cross-section. The cavity opening 116 is sized and shaped such that it is smaller than the distal portion 124 of the flange 122, so that an upper surface 114*b* of the cavity overlaps the distal portion 124 to retain the distal portion 124 within the cavity 114. The distal portion 124 is sized and shaped such that it is moveable within the cavity 114 parallel to the support surface 112, due to the bottom surface 114*a* of the cavity 114 being parallel to the support surface 112. The proximal portion 126 is sized and shaped such that it is moveable within the cavity opening 116 so as to permit movement of the distal portion 124 within the cavity 114.

In use, when the tube retaining member 120 is attached to the base member 110 via the flange 122, the tube retaining member 120 may move relative to the base member 110 in any direction parallel to the support surface 112 of the base member 110. For example, the tube retaining member 120 may move in mutually orthogonal directions as indicated by arrows 1001 in FIG. 5.

Indeed, in other embodiments, any means may be used to moveably attach the tube retaining member 120 and the base member 110 so long as the tube retaining member 120 may move relative to the base member 110. For example, the base member may include a flange and the tube retaining member may include a cavity for receiving the flange of the base member. In another example, the cavity may be shaped such to permit the tube retaining member to rotate relative to the base member about an axis perpendicular to the support surface of the base member. In yet another example, the base member may include a slot and the tube retaining member may include a corresponding projection such that the tube retaining member may move relative to the base member within the slot of the base member.

The tube retaining member 120 includes a tube receiving portion 130 configured to receive and retain a tube (not shown) which is inserted into the patient such that, when the tube is retained by the tube retaining member 120, the tube may move relative to the base member 110 in a direction substantially parallel to the support surface 112 of the base member 110. In certain embodiments, the tube may be retained by the tube receiving portion 130 such that the tube may move in a direction parallel to its longitudinal axis relative to the tube receiving portion 130. In other embodiments, the tube may be retained by the tube receiving portion 130 such that the tube is fixed to the tube receiving portion 130.

In alternative embodiments, the tube retaining member may further include means suitable for retaining additional components, for example, the tube retaining member may include means for retaining circuitry.

In the embodiment shown in FIG. 1, the tube receiving portion 130 comprises a curved clip 134 positioned between a first straight clip 132 and a second straight clip 136, configured so that the tube is receivable and retainable by the clips 132, 134 and 136. The curved clip 134 is configured to guide a portion of the tube into a curve, e.g a U-shape. A U-shape is conventional to certain cannulation attachment procedures as it is desired for a cannula to be attached to the patient's forearm. Thus, as the cannula extends out from the patients hand away from their arm, a U-shape guides the cannula to double back on itself to permit attachment to the patient's forearm. The first clip 132 is positioned axially parallel to one end of the curved clip 134, and the second clip 136 is positioned axially parallel to an opposite end of the curved clip 134. Thus, the tube is guided to double back on itself within the receiving portion 130. The clips 132, 134, 136 may be flexible such that the clips 132, 134, 136 expand to receive and retain the tube. In other embodiments, the clips may be rigid and the tube may flex to be received and retained by the clips.

In certain embodiments, one, two or more straight or curved clips may be used to receive and retain the tube within the tube receiving portion 130.

Indeed, in other embodiments, any suitable means may be used to retain the tube on the tube retaining member 120 such that the tube is guided into a curved shape within the tube retaining member 120. For example, the tube could be taped to the tube retaining member 120, or the tube could be clamped to the tube retaining member 120.

Figure 3:
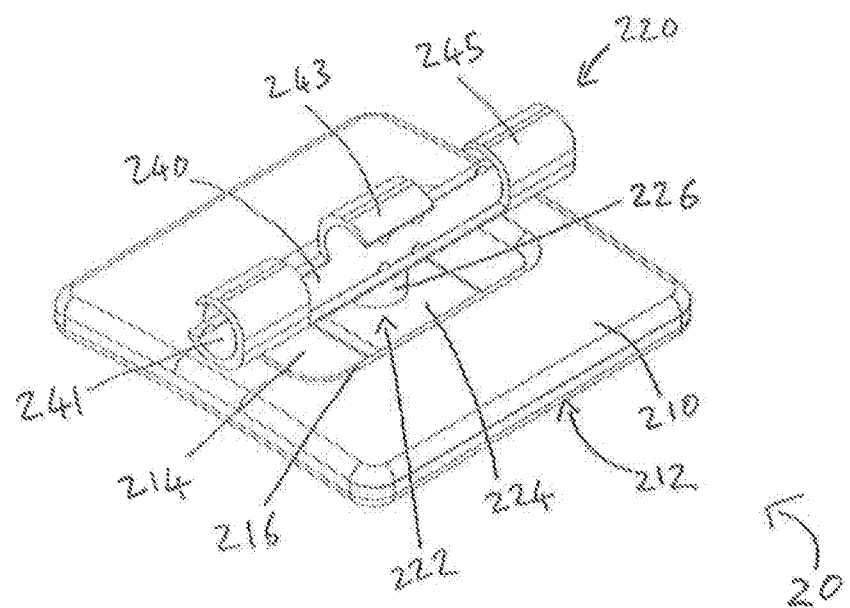
FIG. 3 is a perspective view of a tube stabilising device according to an alternative embodiment of the present invention.

A tube stabilising device 20 according to another embodiment of the present invention is shown in FIG. 3. The tube stabilising device 20 shares features with the tube stabilising device 10 of FIG. 1, and such shared features are numbered using the same last two digits and a differing preceding digit. Differing or additional features of the tube stabilising device 20 of FIG. 3 are described below. In certain embodiments, any or all of the differing or additional features of the tube stabilising device 20 of FIG. 3 may be incorporated into the tube stabilising device 10 of FIG. 1.

Like the tube stabilising device 10 of FIG. 1, the tube stabilising device 20 of FIG. 3 includes a base member 210 and a tube retaining member 220 moveably attached to the base member 210. The base member 210 includes a support surface 212, a cavity 214 and a cavity opening 216. The tube retaining member 220 includes a flange 222 which is received by the cavity 214 and the cavity opening 216 of the base member 210 such to retain the flange 222 within the cavity 214 so that the tube retaining member 220 is moveably attached to the base member 210.

The tube retaining member 220 further includes a tube receiving portion 240 configured to receive and retain a tube (not shown) which is inserted into a patient such that, when the tube is retained by the tube retaining member 220, the tube may move relative to the base member 210 in a direction substantially parallel to the support surface 212 of the base member 210. In certain embodiments, the tube may be retained by the tube receiving portion 240 such that the tube may move in a direction parallel to its longitudinal axis relative to the tube receiving portion 240. In other embodiments, the tube may be retained by the tube receiving portion 240 such that the tube is fixed to the tube receiving portion 240.

The tube receiving portion 240 comprises a first straight clip 241, a second straight clip 243 in axial alignment with the first straight clip 241, and a third straight clip 245 in axial alignment with the second straight clip 243. The tube receiving portion 240 is configured such that the tube is receivable and retainable by each of the first straight clip 241, the second straight clip 243 and the third straight clip 245. When the tube is received by the tube receiving portion 240, the tube remains substantially straight throughout the tube receiving portion 240. That is to say, the longitudinal axis of the tube is parallel to the axis of each of the first straight clip 241, second straight clip 243 and third straight clip 245. The clips 241, 243, 245 may be flexible such that they may expand to receive and retain the tube. In other embodiments, the clips may be rigid and the tube may flex to be received and retained by the clips.

In certain embodiments, one, two or more straight clips may be used to receive and retain the tube within the tube receiving portion 240.

Indeed, in other embodiments, any suitable means may be used to retain the tube on the tube retaining member 220 such that the tube is substantially straight within the tube retaining member 220. For example, the tube could be taped to the tube retaining member 220, or the tube could be clamped to the tube retaining member 220.

In other embodiments, a tube receiving portion may comprise two or more straight clips with angularly offset axes. For example, a second straight clip may be at a 45 degree angle to a first straight clip.

Prior art clinical procedures wherein a tube is inserted into a patient, such as cannulation, use adhesive tape to fix the tube line to a limb of the patient to secure the tube in place. When the patient moves or rotates said limb, unwanted forces may be translated to an entry site of the tube into the patient which may cause bruising and/or swelling at the entry site. Such patient movement is a known cause of procedural failure in cannulation as bruising or swelling may cause occlusion or phlebitis of the patient's veins. Further, such patient movement may lead to cannula failure through dislodgement of the tube from the patient.

In use, the tube stabilising device according to embodiments of the present invention may be fixed to a patient's limb and a cannula extending from a cannula entry site in the patient's limb may be retained by the tube retaining member such that the cannula may move relative to the base member. Thus when the patient moves or rotates their limb, the tube stabilising device absorbs the movement via the cannula moving relative to the base member, thus the tube stabilising device may advantageously reduce the impact of movement by the patient on the cannula entry site. The tube stabilising device may therefore reduce the likelihood of unwanted forces being translated to the cannula entry site and thus may advantageously reduce the likelihood of the patient suffering from bruising or swelling. Further, such a reduction in the likelihood of bruising or swelling may advantageously improve patient comfort and reduce the likelihood of the patient developing occlusion or phlebitis. Furthermore, the tube stabilising device may advantageously reduce the likelihood of the cannula dislodging from the cannula entry site. Consequently, the tube stabilising device may reduce the likelihood of cannulation failure due to the above-mentioned, bruising, swelling and dislodging.

Further still, by reducing the likelihood of patient movement causing cannula failure, the need for re-application of a cannula is reduced. Such a reduction in re-application of cannulas may lead to cost and time savings.

The tube stabilising device is particularly suited to being fixed on or near a joint of the patient, e.g. the patient's wrist, as the tube stabilising device may advantageously absorb movement of the patient about the joint.

Indeed, although the above advantages are related to cannulation, the same advantages may be realised in other clinical procedures wherein a tube is inserted in or otherwise attached to a patient, and subsequently fixed to the patient.

Figure 4:
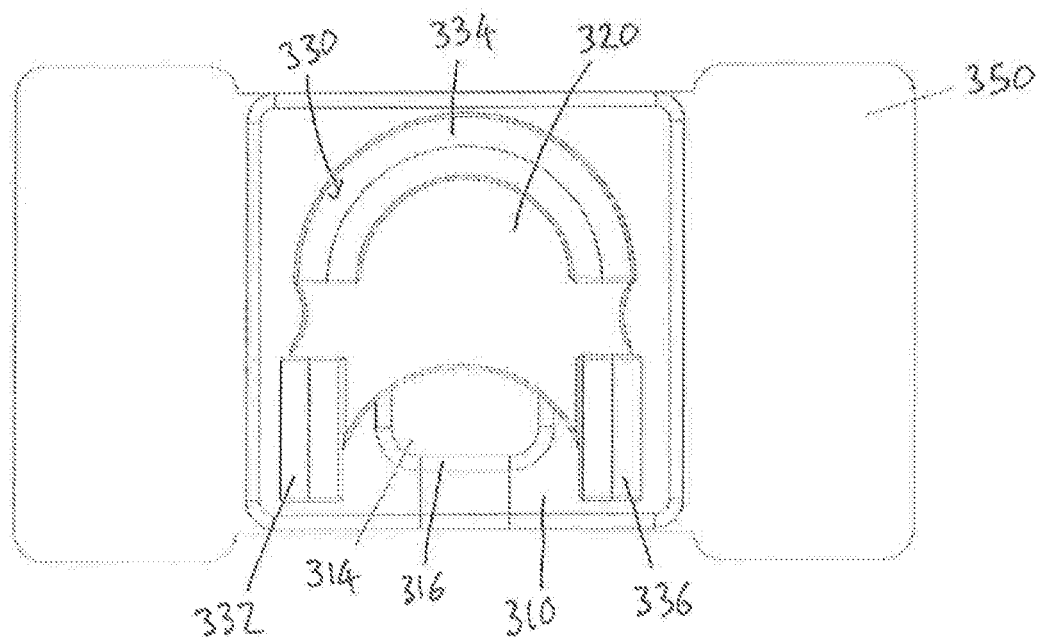
FIG. 4 is a top view of a tube stabilising device according to an alternative embodiment of the present invention.

A tube stabilising device 30 according to another embodiment of the present invention is shown in FIG. 4. The tube stabilising device 30 shares features with the tube stabilising device 10 of FIG. 1, and such shared features are numbered using the same last two digits and a differing preceding digit. Differing or additional features of the tube stabilising device 30 of FIG. 4 are described below. In certain embodiments, any or all of the differing or additional features of the tube stabilising device 30 of FIG. 4 may be incorporated into the tube stabilising device 10 of FIG. 1.

Like the tube stabilising device 10 of FIG. 1, the tube stabilising device 30 of FIG. 4 includes a base member 310 and a tube retaining member 320 moveably attached to the base member 310. The base member 310 includes a support surface 312, a cavity 314 and a cavity opening 316. The tube retaining member 320 includes a flange 322 which is be received by the cavity 314 and the cavity opening 316 of the base member 310 such to retain the flange 322 within the cavity 314 so that the tube retaining member 320 is moveably attached to the base member 310. The tube retaining member 320 further includes a tube receiving portion 330 configured to retain a tube (not shown) which is inserted into a patient such that, when the tube is retained by the tube retaining member 320, the tube may move relative to the base member 310.

The tube stabilising device 30 further includes an adhesive attachment pad 350 attachable to the support surface of the base member 310. The adhesive pad 350 is configured to fix the base member 310 to the patient. By including the adhesive pad 350, the tube stabilising device 30 may advantageously be simply fixed to the patient without the need for any additional adhesive means (e.g. adhesive tape or sutures).

In an alternative embodiment, the tube stabilising device 20 of FIG. 3 may include an adhesive pad similar to the adhesive pad 350 of the tube stabilising device 30 of FIG. 4.

In certain embodiments, the tube stabilising device may be attached to a patient using any means suitable of fixing the base member of the tube stabilising device relative to the patient. For example, the tube stabilising device may be strapped onto the patient or an adhesive may be applied to the tube stabilising device to attach the tube stabilising device to the patient.

In the embodiments discussed above, the flange is coupled to and extends from the tube receiving portion. In alternative embodiments, the flange may be removeably attached to the tube receiving portion via a click on geometry or other suitable means of removable attachment. In such embodiments, the base member may be fixed to a surface and the flange may be received by the base member whereby a user of the tube stabilising device may interchangeably attach either the tube receiving portion 130 of FIGS. 1 and 2, the tube receiving portion 230 of FIG. 3, or the tube receiving portion according to any of the above discussed embodiments.

Figure 5:
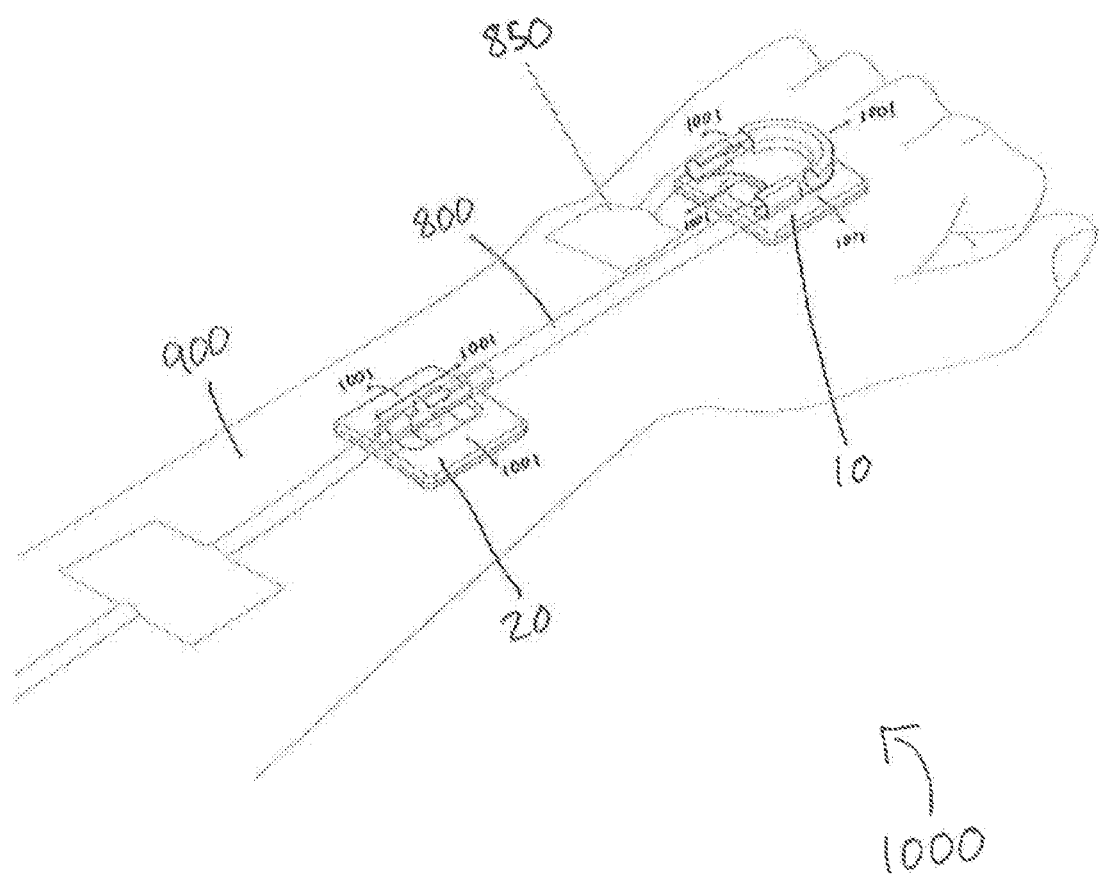
FIG. 5 is a perspective view of a tube stabilising assembly according to an embodiment of the present invention.

A patient's arm 900 having a cannula 800 and a tube stabilising assembly 1000 according to another embodiment of the present invention is shown in FIG. 5. The tube stabilising assembly 1000 includes the tube stabilising device 10 of FIG. 1 and the tube stabilising device 20 of FIG. 3. The cannula 800 extends from a cannula entry site 850 on the patient's arm 900 between the hand and forearm, extending towards a distal end of the patient's arm 900. In the embodiment shown in FIG. 5, the tube stabilising device 10 is fixed to the patient's hand via the support surface 112 of the base member 110 adjacent to the cannula entry site 850. The tube stabilising device 30 is fixed to the patient's forearm via the support surface 212 of the base member 210.

The cannula 800 may be received and retained by the tube stabilising device 10 such that the cannula 800 remains substantially straight through the first straight clip 132 and is guided into a U-shape about the curved clip 134 such that the cannula 800 doubles back on itself to be substantially straight through the second straight clip 136 to extend towards the patient's forearm. The cannula 800 may be received and retained by the tube stabilising device 20 such that the cannula 800 remains substantially straight through the tube receiving portion 240 of the tube stabilising device 20.

In use, the cannula 800 may move within the tube stabilising assembly 1000 relative to the base member 110 of the tube stabilising device 10 and the base member 210 of the tube stabilising device 20. As such, the tube stabilising assembly 1000 advantageously reduces the impact of movement of the patient's arm 900 on the cannula entry site 850.

Indeed, the cannula may extend from a cannula entry site at any suitable location on the patient, e.g. the dorsum of the patient's foot, and along any of the patient's limbs, e.g. the patient's lower leg, or across any of the patient's joints, e.g. the patient's ankle.

In other embodiments, the tube stabilising assembly 1000 may include one, two or more of the tube stabilising device according to embodiments of the present invention to support the cannula 800.

In certain embodiments, the tube stabilising device may comprise a rigid material. For example, the tube stabilising device may comprise a metal.

In certain embodiments, the tube stabilising device may comprise an elastic material. For example, the tube stabilising device may comprise a polymer.

In other embodiments, the tube stabilising device may comprise paper or card.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A tube stabilising device for a tube attached to a patient, comprising:
    a base member fixable to a surface, the base member having a support surface for supporting the base member on a surface of the patient; and
    a tube retaining member;
    wherein the base member includes a cavity configured to receive a flange of the tube retaining member such that, when received, the flange is retained by the base member, the tube retaining member is moveably attached to the base member so as to be moveable in at least two mutually orthogonal directions substantially parallel to the support surface, and the flange is moveable within the cavity in any direction parallel to the support surface;
    the tube retaining member being configured to retain a tube extending from the patient such that, when retained, the tube is moveable relative to the base member.

2. A tube stabilising device according to claim 1, wherein the tube comprises a cannula or catheter.

3. A tube stabilising device according to claim 1, wherein the surface, on which the base member is fixable, comprises a surface of a patient.

4. A tube stabilising device according to claim 1, wherein the tube retaining member includes a removeable portion, the removeable portion being removeably attachable to the flange of the tube retaining member.

5. A tube stabilising device according to claim 1, wherein the tube retaining member includes receiving means configured to receive a portion of the tube.

6. A tube stabilising device according to claim 5, wherein the receiving means of the tube retaining member includes a substantially straight portion such that, when the tube is received by the tube retaining member, the tube is substantially straight throughout the straight portion of the receiving means.

7. A tube stabilising device according to claim 6, wherein the straight portion of the receiving means includes one or more clips configured to receive and retain the tube within the tube retaining member.

8. A tube stabilising device according to claim 7, wherein the one or more clips includes a clip that is part-cylindrical.

9. A tube stabilising device according to claim 6, wherein the straight portion of the receiving means includes two or more clips along the same axis configured such that, when the tube is received by the tube retaining member, the tube is substantially straight between the two or more clips.

10. A tube stabilising device according to claim 5, wherein the receiving means includes a curved guide configured such that, when the tube is received by the receiving means, the tube is curved around the curved guide.

11. A tube stabilising device according to claim 10, wherein the curved guide includes one or more clips configured to receive and retain the tube within the tube retaining member.

12. A tube stabilising device according to claim 11, wherein the one or more clips of the curved guide comprise one or more curved clips.

13. A tube stabilising device according to claim 12, wherein the one or more curved clips includes a curved clip that is part-cylindrical.

14. A tube stabilising device according to claim 11, wherein the one or more clips includes a clip that is part-cylindrical.

15. A tube stabilising device according to claim 10, wherein the receiving means includes a straight portion adjacent to a first end of the curved portion.

16. A tube stabilising device according to claim 15, wherein the receiving means includes a straight portion adjacent to an end opposite the first end of the curved portion.

17. A tube stabilising device according to claim 10, wherein the curved guide comprises a U-shaped curve configured such that, when the tube is received by the receiving means, the tube is U-shaped within the curved guide.

18. A tube stabilising device according to claim 1, wherein the tube retaining member includes a removeable portion, the removeable portion being removeably attachable to the flange of the tube retaining member, wherein the tube retaining member includes receiving means configured to receive a portion of the tube, and wherein the removeable portion of the tube retaining member comprises the receiving means.

19. A tube stabilising device according to claim 1, wherein the base member is fixable to the patient via an adhesive.

20. A tube stabilising device according to claim 19, wherein the adhesive comprises an adhesive attachment pad.

21. A tube stabilising assembly for a tube inserted into a patient, comprising:
    a first tube stabilising device comprising:
        a base member fixable to a surface, the base member having a support surface for supporting the base member on a surface of the patient; and
        a tube retaining member;
        wherein the base member includes a cavity configured to receive a flange of the tube retaining member such that, when received, the flange is retained by the base member, the tube retaining member is moveably attached to the base member and the flange is moveable within the cavity in any direction parallel to the support surface;
        the tube retaining member being configured to retain a tube extending from the patient such that, when retained, the tube is moveable relative to the base member; and one or more further tube stabilising device, each of the one or more further tube stabilising device comprising:
    a base member fixable to a surface, the base member having a support surface for supporting the base member on a surface of the patient; and
    a tube retaining member;

wherein the base member includes a cavity configured to receive a flange of the tube retaining member such that, when received, the flange is retained by the base member, the tube retaining member is moveably attached to the base member so as to be moveable in at least two mutually orthogonal directions substantially parallel to the support surface, and the flange is moveable within the cavity in any direction parallel to the support surface;

the tube retaining member being configured to retain a tube extending from the patient such that, when retained, the tube is moveable relative to the base member;

wherein the tube stabilising assembly is configured such that a tube exiting a patient's body is retainable by the first tube stabilising device and the one or more further tube stabilising device.

22. A tube stabilising assembly for a tube inserted into a patient, comprising:

(i) a first tube stabilising device comprising:
a base member fixable to a surface, the base member having a support surface for supporting the base member on a surface of the patient; and
a tube retaining member;
wherein the base member includes a cavity configured to receive a flange of the tube retaining member such that, when received, the flange is retained by the base member, the tube retaining member is moveably attached to the base member and the flange is moveable within the cavity in any direction parallel to the support surface;
the tube retaining member being configured to retain a tube extending from the patient such that, when retained, the tube is moveable relative to the base member;
wherein the tube retaining member includes receiving means configured to receive a portion of the tube;
wherein the receiving means includes a curved guide configured such that, when the tube is received by the receiving means, the tube is curved around the curved guide; and (ii) a second tube stabilising device comprising:
a base member fixable to a surface, the base member having a support surface for supporting the base member on a surface of the patient; and
a tube retaining member;
wherein the base member includes a cavity configured to receive a flange of the tube retaining member such that, when received, the flange is retained by the base member, the tube retaining member is moveably attached to the base member and the flange is moveable within the cavity in any direction parallel to the support surface;
the tube retaining member being configured to retain a tube extending from the patient such that, when retained, the tube is moveable relative to the base member;
wherein the tube retaining member includes receiving means configured to receive a portion of the tube;
wherein the receiving means of the tube retaining member includes a substantially straight portion such that, when the tube is received by the tube retaining member, the tube is substantially straight throughout the straight portion of the receiving means;
wherein the tube stabilising assembly is configured such that a tube exiting a patient's body is retainable by the first tube stabilising device and the second tube stabilising device.

23. A tube stabilising assembly according to claim 22, wherein the first tube stabilising device is configured to attach to a patient's hand adjacent to an exit point of a tube from the patient's hand, and the second tube stabilising device is configured to attach to the patient's forearm, the tube stabilising assembly being configured such that the tube is moveable within the assembly relative to the patient.

* * * * *